(12) United States Patent
Murphy et al.

(10) Patent No.: US 9,709,491 B1
(45) Date of Patent: Jul. 18, 2017

(54) SYSTEM AND METHOD FOR MEASURING AEROSOL OR TRACE SPECIES

(71) Applicant: The United States of America, represented by the Secretary of Commerce, Washington, DC (US)

(72) Inventors: Daniel M. Murphy, Boulder, CO (US); Timothy D. Gordon, Boulder, CO (US)

(73) Assignee: The United States of America, Washington, DC (US)

( * ) Notice: Subject to any disclaimer, the term of this patent is extended or adjusted under 35 U.S.C. 154(b) by 11 days.

(21) Appl. No.: 15/082,112

(22) Filed: Mar. 28, 2016

(51) Int. Cl.
*G01N 21/00* (2006.01)
*G01N 21/47* (2006.01)

(52) U.S. Cl.
CPC ... *G01N 21/474* (2013.01); *G01N 2021/4742* (2013.01)

(58) Field of Classification Search
CPC .. G01N 21/39; G01N 21/3504; G01N 21/031; G01N 2021/399; G01N 2021/391; G01N 33/497; G01N 21/3581; G01N 2201/06113; G01N 21/1702; G01N 21/33; G01N 21/71; G01N 21/718; G01N 33/0057
See application file for complete search history.

(56) References Cited

U.S. PATENT DOCUMENTS

| | | | |
|---|---|---|---|
| 3,967,933 A | 7/1976 | Etess et al. | |
| 4,018,562 A | 4/1977 | Parks et al. | |
| 4,066,409 A | 1/1978 | Fine | |
| 4,687,337 A | 8/1987 | Stewart et al. | |
| 4,717,675 A | 1/1988 | Sievers et al. | |
| 4,822,564 A | 4/1989 | Howard | |
| 5,059,790 A * | 10/1991 | Klainer | G01N 21/7703 250/227.21 |
| 5,297,156 A | 3/1994 | Deacon | |
| 5,804,702 A | 9/1998 | Hovde et al. | |
| 5,818,598 A | 10/1998 | Kebabian | |
| 6,346,419 B1 | 2/2002 | Ryerson et al. | |

(Continued)

FOREIGN PATENT DOCUMENTS

WO  2006114766  11/2006

OTHER PUBLICATIONS

Fahey, D.; Eubank, C.; Hübler, G.; Fehsenfeld, F. Evaluation of a catalytic reduction technique for the measurement of total reactive odd-nitrogen NOy in the atmosphere. Journal of Atmospheric Chemistry 1985, 3, 435-468.

(Continued)

*Primary Examiner* — Michael P Stafira
(74) *Attorney, Agent, or Firm* — Robert Platt Bell (57) ABSTRACT

Embodiments of the present invention relates to a system for measuring trace species in a sample gas. The present invention uses an open-path configuration including an optical cell with mirrors at each end, a long slotted rod with holes in the end for an optical bean to pass through, and a slotted tube surrounding the slotted rod such that air can pass through the rod in a transverse direction when the slots are aligned. Embodiments of the present invention further includes a flow configuration for purging sample gas from the optical cell, and cleaning mirrors, with calibrated or zero air through inlets in front of each mirror.

20 Claims, 8 Drawing Sheets

(56) References Cited

U.S. PATENT DOCUMENTS

| | | | | |
|---|---|---|---|---|
| 6,421,127 | B1* | 7/2002 | McAndrew | G01J 3/0259 356/246 |
| 7,045,359 | B2 | 5/2006 | Birks et al. | |
| 7,301,639 | B1 | 11/2007 | Kebabian et al. | |
| 7,477,377 | B2* | 1/2009 | Silver | G01N 21/031 356/246 |
| 7,755,767 | B2* | 7/2010 | Ruth | G01J 3/42 356/454 |
| 7,765,713 | B2 | 8/2010 | Ehrhard et al. | |
| 8,174,691 | B1 | 5/2012 | Horton et al. | |
| 8,508,740 | B2* | 8/2013 | Richter | G01N 21/031 356/440 |
| 8,654,334 | B1 | 2/2014 | Gupta et al. | |
| 8,846,407 | B2 | 9/2014 | Hargrove | |
| 8,885,167 | B2* | 11/2014 | Kachanov | H01S 5/0028 356/437 |
| 9,121,838 | B2* | 9/2015 | Farooq | G01N 33/0054 |
| 9,151,708 | B2* | 10/2015 | Lehmann | G01N 21/0303 |
| 2009/0120212 | A1 | 5/2009 | Hargrove et al. | |
| 2011/0027899 | A1 | 2/2011 | Hargrove et al. | |
| 2012/0002212 | A1 | 1/2012 | Chandler et al. | |
| 2012/0113426 | A1 | 5/2012 | Rao et al. | |
| 2013/0017618 | A1 | 1/2013 | Hargrove et al. | |
| 2015/0377850 | A1 | 12/2015 | Brown et al. | |

OTHER PUBLICATIONS

Williams, E. J.; Baumann, K.; Roberts, J. M.; Bertman, S. B.; Norton, R. B.; Fehsenfeld, F. C.; Springston, S. R.; Nunnermacker, L. J.; Newman, L.; Olszyna, K.; Meagher, J.; Hartsell, B.; Edgerton, E.; Pearson, J. R.; Rodgers, M. O. Intercomparison of ground-based NOy measurement techniques. Journal of Geophysical Research: Atmospheres 1998, 103, 22261-22280.
Crosley, D. R. NOy Blue Ribbon panel. Journal of Geophysical Research: Atmospheres 1996, 101, 2049-2052.
Kliner, D. A. V.; Daube, B. C.; Burley, J. D.; Wofsy, S. C. Laboratory investigation of the catalytic reduction technique for measurement of atmospheric NOy. Journal of Geophysical Research: Atmospheres 1997, 102, 10759-10776.
Neuman, J. A.; Huey, L. G.; Ryerson, T. B.; Fahey, D. W. Study of Inlet Materials for Sampling Atmospheric Nitric Acid. Environmental Science & Technology 1999, 33, 1133-1136.
Dubé, W. P.; Brown, S. S.; Osthoff, H. D.; Nunley, M. R.; Ciciora, S. J.; Paris, M. W.; McLaughlin, R. J.; Ravishankara, A. R. Aircraft instrument for simultaneous, in situ measurement of NO3 and N2O5 via pulsed cavity ring-down spectroscopy. Review of Scientific Instruments 2006, 77.
Wooldridge, P. J.; Perring, A. E.; Bertram, T. H.; Flocke, F. M.; Roberts, J. M.; Singh, H. B.; Huey, L. G.; Thornton, J. A.; Wolfe, G. M.; Murphy, J. G.; Fry, J. L.; Rollins, A. W.; LaFranchi, B. W.; Cohen, R. C. Total Peroxy Nitrates in the atmosphere: the Thermal Dissociation-Laser Induced Fluorescence (TD-LIF) technique and comparisons to speciated PAN measurements. Atmospheric Measurement Techniques 2010, 3, 593-607.
Di Carlo, P.; Aruffo, E.; Busilacchio, M.; Giammaria, F.; Dari-Salisburgo, C.; Biancofiore, F.; Visconti, G.; Lee, J.; Moller, S.; Reeves, C. E.; Bauguitte, S.; Forster, G.; Jones, R. L.; Ouyang, B. Aircraft based four-channel thermal dissociation laser induced fluorescence instrument for simultaneous measurements of NO2, total peroxy nitrate, total alkyl nitrate, and HNO3. Atmospheric Measurement Techniques 2013, 6, 971-980.
Pérez, I. M.; Wooldridge, P. J.; Cohen, R. C. Laboratory evaluation of a novel thermal dissociation chemiluminescence method for in situ detection of nitrous acid. Atmospheric Environment 2007, 41, 3993-4001.
Thaler, R. D.; Mielke, L. H.; Osthoff, H. D. Quantification of Nitryl Chloride at Part Per Trillion Mixing Ratios by Thermal Dissociation Cavity Ring-Down Spectroscopy. Analytical Chemistry 2011, 83, 2761-2766.
Day, D. A.; Wooldridge, P. J.; Dillon, M. B.; Thornton, J. A.; Cohen, R. C. A thermal dissociation laser-induced fluorescence instrument for in situ detection of NO2, peroxy nitrates, alkyl nitrates, and HNO3. Journal of Geophysical Research: Atmospheres 2002, 107, ACH 4-1-ACH 4-14.
Mazurenka, M. I.; Fawcett, B. L.; Elks, J. M.; Shallcross, D. E.; Orr-Ewing, A. J. 410-nm diode laser cavity ring-down spectroscopy for trace detection of NO2. Chemical Physics Letters 2003, 367, 1-9.
Wada, R.; Orr-Ewing, A. J. Continuous wave cavity ring-down spectroscopy measurement of NO2 mixing ratios in ambient air. Analyst 2005, 130, 1595-1600.
Hargrove, J.; Wang, L.; Muyskens, K.; Muyskens, M.; Medina, D.; Zaide, S.; Zhang, J. Cavity Ring-Down Spectroscopy of Ambient NO2 with Quantification and Elimination of Interferences. Environmental Science & Technology 2006, 40, 7868-7873.
Castellanos, P.; Luke, W. T.; Kelley, P.; Stehr, J. W.; Ehrman, S. H.; Dickerson, R. R. Modification of a commercial cavity ring-down spectroscopy NO2 detector for enhanced sensitivity. Review of Scientific Instruments 2009, 80.
Fuchs, H.; Dubé, W. P.; Lerner, B. M.; Wagner, N. L.; Williams, E. J.; Brown, S. S. A Sensitive and Versatile Detector for Atmospheric NO2 and NOx Based on Blue Diode Laser Cavity Ring-Down Spectroscopy. Environmental Science & Technology 2009, 43, 7831-7836, PMID: 19921901.
Washenfelder, R. A.; Wagner, N. L.; Dubé, W. P.; Brown, S. S. Measurement of Atmospheric Ozone by Cavity Ring-down Spectroscopy. Environmental Science & Technology 2011, 45, 2938-2944.
Wagner, N. L.; Dubé, W. P.; Washenfelder, R. A.; Young, C. J.; Pollack, I. B.; Ryerson, T. B.; Brown, S. S. Diode laser-based cavity ring-down instrument for NO3, N2O5, NO, NO2 and O3 from aircraft. Atmospheric Measurement Techniques 2011, 4, 1227-1240.
Rollins, A. W.; Smith, J. D.; Wilson, K. R.; Cohen, R. C. Real Time In Situ Detection of Organic Nitrates in Atmospheric Aerosols. Environmental Science & Technology 2010, 44, 5540-5545.
Johnston, H. S.; Cantrell, C. A.; Calvert, J. G. Unimolecular decomposition of NO3 to form NO and O2 and a review of N2O5/NO3 kinetics. Journal of Geophysical Research: Atmospheres 1986, 91, 5159-5172.
Reisen, F.; Arey, J. Atmospheric Reactions Influence Seasonal PAH and Nitro-PAH Concentrations in the Los Angeles Basin. Environmental Science & Technology 2005, 39, 64-73.
Axson, J. L.; Washenfelder, R. A.; Kahan, T. F.; Young, C. J.; Vaida, V.; Brown, S. S. Absolute ozone absorption cross section in the Huggins Chappuis minimum (350-470 nm) at 296 K. Atmospheric Chemistry and Physics 2011, 11, 11581-11590.
Slusher, D. L.; Huey, L. G.; Tanner, D. J.; Flocke, F. M.; Roberts, J. M. A thermal dissociation-chemical ionization mass spectrometry (TD-CIMS) technique for the simultaneous measurement of peroxyacyl nitrates and dinitrogen pentoxide. Journal of Geophysical Research: Atmospheres 2004, 109.
Helmig, D.; Thompson, C. R.; Evans, J.; Boylan, P.; Hueber, J.; Park, J.-H. Highly Elevated Atmospheric Levels of Volatile Organic Compounds in the Uintah Basin, Utah. Environmental Science & Technology 2014, in press.
McClenny, W. A., et al., Preparing to measure the effects of the NOx SIP Call—Methods for ambient air monitoring of NO, NO2, NOy, and individual NOz species, Journal of the Air & Waste Management Association 2002, 52, 542-562.
Day, et al., "a thermal disassociation laser-induced fluorescent instrument for in situ detection of NO2, peroxy nitrates, alkyl nitrates and HN03" Journal of Geophysical Research, Mar. 21, 2002, vol. 107 No. D4.
PCT Search Report PCT/US2015/032535, published Aug. 19, 2015.
Anderson and Ogren, Determining Aerosol Radiative Properties Using the TSI 3563 Integrating Nephelometer, Aerosol Science and Technology, 29:57-69 (1998).
LI-7700 Open Path CH4 Analyzer, Fast Atmospheric Methane Measurements, LI-CORE Biosciences, Nov. 2010.
SenseAir TN-010 Technical Note, Theory of Calibration for SensAir IR gas sensors, Jul. 2000.

(56) References Cited

OTHER PUBLICATIONS

SPEC Inc.—Cloud Extinctiometer http://www.specinc.com/cloud-extinctiometer (c) 2102.
Wada et al, Measurement of IO radical concentrations in the marine boundary layer using a cavity ring-down spectrometer, Journal of Atmospheric Chemistry (2007) 58:69-87.
Picarro Cavity Ringdown Spectrometer, http://www.picarro.com/technology/cavity_ring_down_spectroscopy, (c) 2016, printed Feb. 19, 2016.
Los Gatos Cavity Ringdown Spectroscopy, http://www.lgrinc.com/resources/crd-spectroscopy.php, (c) 2016, printed Feb. 19, 2016.
Aerodyne Research, Inc.—Astigmatic Multipass Cell, http://www.aerodyne.com/products/astigmatic-multipass-absorption-cells, Printed Feb. 19, 2016.
SpectraSensors Tunable Diode Laser, http://www.spectrasensors.com/technology/, Printed Feb. 19, 2016.
Tiger Optics Cavity Ring-Down Spectroscopy, http://www.tigeroptics.com/app/tigeroptics/info/cavity_ring_down_spectroscopy.php, Printed Feb. 19, 2016.
Final Report, NASA GSFC STTR Contract No. NAS5-96042, "An optical Extictiometer for Cloud Radiation Measurements", Feb. 2000.
Stroga, et al, High spectral resolution lidar to measure optical scattering properties of atmospheric aerosols, Applied Optics, Dec. 1, 1983, vol. 22, No. 23.

\* cited by examiner

SYSTEM AND METHOD FOR MEASURING AEROSOL OR TRACE SPECIES

STATEMENT REGARDING FEDERAL RIGHTS

The invention described herein was made with support from the National Oceanic and Atmospheric Administration (NOAA) of the United States Department of Commerce. The United States Government has certain rights in the invention.

FIELD OF THE INVENTION

The present disclosure relates generally to absorption spectroscopy, and more particularly, to a system for measuring light scattering and absorption by aerosols using ringdown spectroscopy.

BACKGROUND OF THE INVENTION

Natural aerosols (e.g., dust, sea salt, volcanic ash) and anthropogenic aerosols (e.g., particulate matter from fossil fuel combustion) perturb the earth's climate through direct effects (scattering or absorbing solar radiation) and indirectly by modifying cloud properties. However, the uncertainty in aerosol radiative forcing is high, and the ability to frame effective climate change policies depends on reducing this uncertainty by a factor of 3 to 10. Achieving this goal will require improvements in measuring the scattering and absorption properties of aerosols, especially in regions that are difficult to characterize with existing instruments (e.g., in or near clouds and coarse particle-dominated regions).

Light scattering due to aerosols increases rapidly at humidities above 90%. While measurements of humidified scattering have been made with wet nephelometers at relative humidities (RH) of up to 85%, measuring scattering at higher RH has proven technically challenging. Cavity ringdown spectrometers (CRDSs) have been used to quantify aerosol extinction (scattering and absorption) in humidities up to RH≈90%. But at very high humidities, as found in and near clouds, existing CRDSs perform poorly, diverging significantly from theoretically predicted extinction coefficients. It is difficult to maintain humidities greater than 90-95% in CRDS without condensational losses. In addition, significant loss of larger particles can occur due to impact losses with CRDS inlet tubing. Furthermore, humidity may be enhanced for tens of kilometers around clouds, and 30 to 60% of the global areas that are considered cloud-free may in fact include regions of high humidity. Because most satellite retrievals tend to be biased toward data that is far from clouds, some fraction of these "twilight zones" may not be included in existing satellite retrievals, which may degrade the accuracy of aerosol direct forcing estimates.

In situ measurements of aerosol extinction obtained during atmospheric profiles could help constrain ground- and satellite-derived aerosol optical depth (AOD) retrievals. The need for such constraints is acute not only in and near clouds but also in regions with high coarse dust burdens (e.g., continental-scale regions downwind of north African dust plumes). Such regions constitute an important source of uncertainty in estimates of radiative effects. Accordingly, there is a need for an instrument capable of making in situ aerosol extinction measurements in dusty and highly humid environments.

There is also a need for an instrument capable of characterizing gases that are too reactive or otherwise unsuitable to be measured with a closed instrument. Instruments used to measure particles and gases are usually calibrated and zeroed with calibrated or clean air. But some measurements need to be made in the open; in such instances the sample cannot be plumbed into an instrument. Calibrations and zeros are not easily achieved when the instrument is open to the ambient atmosphere. However, without calibrations and zeros, it is difficult to distinguish real changes in the sample of interest from artifactual changes in the reflectivity of the mirrors, windows, or other changes in the system.

BRIEF SUMMARY OF THE INVENTION

Embodiments of the present invention relate to a system including an open-path cavity to measure extinction of highly humidified and/or coarse aerosol by allowing the aerosol to flow freely through an optical cavity without any intervening inlet or tubing. An open-path aerosol extinction system in accordance with embodiments of the present invention is capable of isolating the optical cavity from wind and rain while still providing an open path for the aerosol through the optical cavity. Accordingly, embodiments of the present invention relates to a system for measuring trace species in a sample gas, including a laser source for emitting continuous wave laser beam; an optical isolator for allowing transmission of the laser beam in one direction; a plurality of input mirrors for directing the laser beam into an optical cavity; a first curved mirror located at a first end and a second curved mirror located at a second end, wherein the first and second curved mirrors face each other along a common optical axis to form the optical cavity; a rod positioned between the first and second curved mirrors, wherein the longitudinal axis of the rod is aligned with the optical axis, wherein the rod comprises a linear slot encompassing the optical cavity, wherein the linear slot extends along a predetermined length on the rod along the longitudinal axis, wherein the linear slot is capable of receiving the sample gas, and wherein the rod comprises a first aperture and a second aperture to allow the laser beam received from the plurality of input mirrors to pass through the rod along the optical axis; a tube concentric with and surrounding the rod, wherein the tube comprises a first linear slot and second linear slot, wherein the first and second linear slot oppose each other to form a pass-through slot; and a photodetector for measuring light transmitted through the optical cavity and producing a corresponding signal.

More particularly, the rod comprising the linear slot further comprises an optical sensing region along the optical axis within the linear slot, and wherein the optical sensing region and the walls of the linear slot are separated by a predetermined distance.

In one aspect of the present invention, the tube is capable of concentric rotation around the rod, and wherein the first and second slots are capable of simultaneously aligning with the linear slot on the rod. In another aspect of the present invention, the tube is capable of concentric rotation around the rod such that the first and second slots are capable of simultaneously misaligning with the linear slot on the rod to seal the linear slot on the rod from ambient air. More particularly, the tube is capable of concentric rotation of about 90 degrees around the rod.

In one aspect of the present invention, the optical cell further comprises a first mirror chamber for accommodating the first curved mirror and a second mirror chamber for accommodating the second curved mirror; and a first and second inlet ports located on the first and second mirror chambers, wherein the first and second inlet ports are capable of receiving and directing calibrated gas in front of the first and second curved mirrors. In some embodiments of the present invention, the optical cell further includes at least one exit port located at the center of the tube and perpendicular to the first and second slots for purging the calibrated gas.

Embodiments in accordance with the present invention further comprises a fiber collimator located behind the second curved mirror for collecting laser beam exiting the optical cavity through the second curved mirror, wherein the collimator focuses the collected laser beam into a fiber optic cable, and wherein the fiber optic cable transmits the focused laser beam to the photodetector.

Some embodiments of the present invention further comprises a processor, responsive to said signal from the photodetector, for calculating the decay rate of the optical cavity, wherein the processor, responsive to said decay rate, determines the level of trace species in said sample gas, and wherein the processor synchronizes the measuring of the transmitted light by the photodetector with operation of the laser source.

Embodiments of the system in accordance with the present invention further comprises a housing for accommodating the first and second chamber, the rod and the tube, wherein the housing comprises a vertically oriented slot; at least one fan positioned at a first end of the housing to draw ambient air from a second end of the housing through the vertically oriented slot in the housing, wherein the second end of the housing is open to the ambient air; and a flow straightener positioned at the second end of the housing, wherein the flow straighteners is capable of reducing turbulence in the optical cavity.

Other aspects of the present invention relates to an open-path optical cell for measuring trace species in a sample gas, including a first mirror chamber comprising a first curved mirror located at a first end of the optical cell and a second mirror chamber comprising a second curved mirror located at a second end of the optical cell, wherein the first and second curved mirrors face each other along a common optical axis to form an optical cavity; a first and second inlet ports located on the first and second mirror chambers, wherein the first and second inlet ports are capable of receiving and directing calibrated gas in front of the first and second curved mirrors; a rod positioned between the first and second curved mirrors, wherein the longitudinal axis of the rod is aligned with the optical axis, wherein the rod comprises a linear slot encompassing the optical cavity and extending along a predetermined length on the rod along the longitudinal axis, wherein the linear slot is capable of receiving the sample gas, wherein the rod comprises a first aperture to receive the laser beam from the first curved mirror and a second aperture to output the laser beam along the longitudinal axis to the second curved mirror, and wherein the first and second apertures allow the laser beam to pass through the rod along the optical axis; and a tube concentric with and surrounding the rod, wherein the tube comprises a first linear slot opposing a second linear slot to form a pass through slot. More particularly, the rod including the linear slot further comprises an optical sensing region along the optical axis within the linear slot, and wherein the optical sensing region is not perturbed by the walls of the linear slot.

Another embodiment of the present invention relates to a system for measuring trace species in a sample gas, which comprises a light source for emitting an optical beam; a first mirror chamber comprising a first curved mirror, wherein the first curved mirror is positioned to receive the optical beam; a second mirror chamber comprising a second curved mirror, wherein the first and second curved mirrors face each other along a common optical axis to form an optical cavity; a first and second inlet ports located on the first and second mirror chambers, wherein the first and second inlet ports are capable of receiving and directing calibrated gas in front of the first and second curved mirrors; a first and second plates for mounting the light source and the first and second mirror chambers, wherein the first and second plates align the light source and the first and second curved mirrors along the optical axis; a sample cavity formed between the first and second plates for receiving the sample gas, wherein the longitudinal axis of the sample cavity is aligned with the optical axis, wherein the sample cavity comprises a linear slot encompassing the optical cavity and extending along a predetermined length along the longitudinal axis, wherein the linear slot is capable of receiving the sample gas, wherein the sample cavity comprises a first aperture to receive the laser beam from the first curved mirror and a second aperture to output the laser beam along the longitudinal axis to the second curved mirror, and wherein the first and second apertures allow the laser beam to pass through the sample cavity along the optical axis; a tube surrounding the first and second plates forming the sample cavity, wherein the tube comprises a first linear slot opposing a second linear slot to form a pass through slot; and a photodetector mounted on the first plate for measuring light transmitted through the optical cavity and producing a corresponding signal.

DETAILED DESCRIPTION OF THE INVENTION

Embodiments of the present invention relate to a system for measuring trace species in a sample gas. The present invention uses an open-path cavity to measure aerosol extinction in conditions that are difficult to quantify with typical closed path cavity instruments. Embodiments of the present invention are used to characterize the extinction of highly humidified and/or coarse aerosol by allowing the aerosol to flow freely through the optical cavity without any intervening inlet or tubing. An open-path aerosol extinction system in accordance with embodiments of the present invention is capable of isolating the optical cavity from wind and rain while still providing an open path for the aerosol through the optical cavity. In embodiments of the present invention, the open-path configuration includes: an optical cell with mirrors at each end; a long slotted rod with holes in the end for an optical beam to pass through; and a slotted tube surrounding the slotted rod such that air can pass through the rod in a transverse direction when the slots are aligned. Embodiments of the present invention further includes a flow configuration for purging sample gas from the optical cell, and preventing mirror contamination, with calibrated or particle-free air through inlets in front of each mirror.

Figure 1:
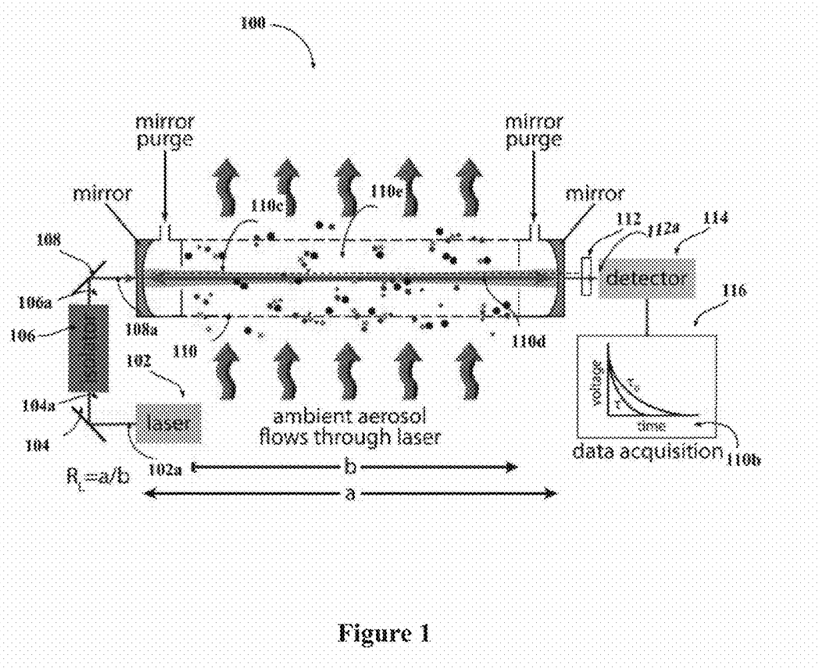
FIG. 1 illustrates an open-path aerosol extinction system for measuring trace species in a sample gas.

Referring now to the drawings, and more particularly, to FIG. 1, there is shown an open-path aerosol extinction system for measuring trace species in a sample gas, generally designated 100, which comprises embodiments of the present invention. Open-path aerosol extinction system 100 includes light source 102, optical isolator 106, optical components 104 and 108, optical cell 110, collimator 112, photodetector 114 and processor 116.

Light source 102 generates the primary optical beam along path 102a. Continuous or pulsed lasers are suitable due to the efficient coupling of light into the ringdown optical cavity. Light source 102 suitably generates light comprising a wavelength corresponding to an optical region of interest in a sample. For gases containing particles, wavelength of light generated by light source 102 corresponds to optical region where information on light extinction can be obtained. For traces gases, wavelength of light generated by light source 102 corresponds to optical region with an absorption feature. In one embodiment of the present invention, light source 102 is a 674 nm diode laser. In another embodiment, light source 102 is a 450 nm diode laser. In yet another embodiment of the present invention, light source 102 is a 450 nm light emitting diode.

Optical isolator 106 is positioned in path 104a of optical beam to reduce optical feedback caused by back reflections into optical beam along path 104a, and control the polarization of optical beam along path 104a. In one embodiment of the present invention isolator 106 can be a Faraday isolator.

Optical component 104 is placed in front of light source 102 to direct optical beam along path 102a to isolator 106. Optical component 108 is placed in front of isolator 106 to direct optical beam along path 106a to optical cell 110. Optical beam from light source 102 may also be directed to the optical cell 110 by other light directing means such as fiber optic delivery and the like. The optical path from light source 102 to optical cell 110 may also include optics to focus the light, or otherwise improve the coupling of light into the optical cell.

Figure 2:
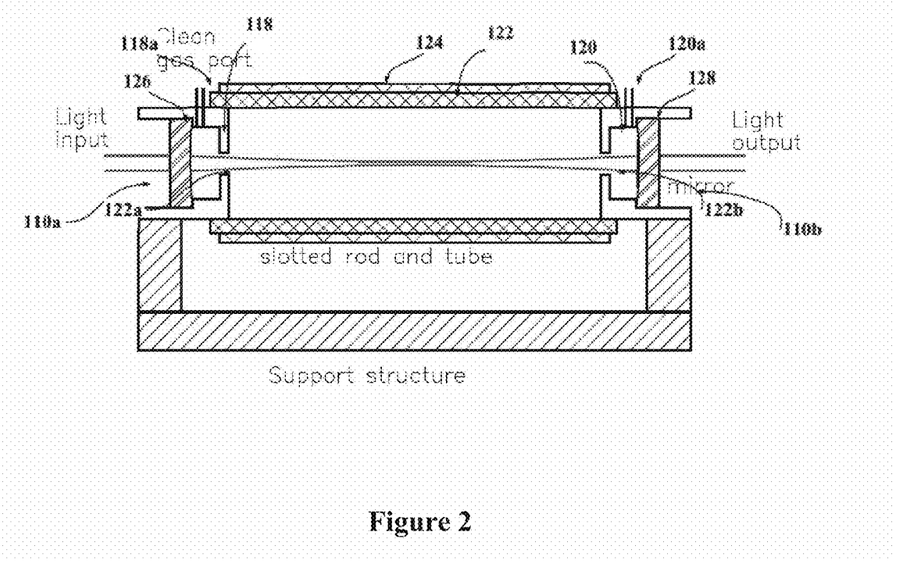
FIG. 2 illustrates an optical cell in accordance with one embodiment of the present invention.

Optical cell 110 includes a linear optical cavity 110e formed between curved entrance mirror 126 and curved output mirror 128, as shown in FIG. 2. In one embodiment of the present invention, curved mirrors 126 and 128 are spherical. In another embodiment of the present invention, curved mirrors 126 and 128 are elliptical. An optical cavity is an optical structure with a hollow core or hollow cross-sectional structure that can be filled with a gas, liquid, or material of differing dielectric properties than the cavity itself. Referring to FIG. 2, optical cell 110 further includes cavity entrance mirror chamber 118, cavity output mirror chamber 120, slotted rod 122, and slotted tube 124.

Cavity entrance mirror chamber 118 is located at the entrance 110a of the optical cell 110 and cavity output mirror chamber 120 is located at the exit 110b of the optical cell 110. Curved entrance mirror 126 is positioned within cavity entrance mirror chamber 118 and curved output mirror 128 is positioned within cavity output mirror chamber 120. Curved entrance mirror 126 and curved output mirror 128 are positioned facing each other along a common optical axis 110c to form linear optical cavity 110e.

In some embodiments of the present invention, curved entrance mirror 126 and curved output mirror 128 are configured to reflect light between one another within linear optical cavity 110e. Curved entrance mirror 126 and curved output mirror 128 are highly reflective so as to minimize light loss within optical cavity 110e of optical cell 110. In an exemplary embodiment of the present invention, curved entrance mirror 126 and curved output mirror 128 are concave dielectric mirrors of 1 meter radius of curvature having a dielectric coating (e.g., Advanced Thin Films, Boulder, Colo., USA) optimized for maximum reflectivity of about 99.9993% at laser wavelength of about 674 nm.

In one embodiment of the present invention, curved mirrors 126 and 128 may include a small area of reflective coating removed to form an aperture positioned at the center of curved mirrors 126 and 128. The aperture may also be positioned off center of the mirror surface. Mirror chambers 118 and 120 include inlet ports 118a and 120a for receiving gas capable of purging optical cell 110. In some embodiments of the present invention, inlet port 118a is positioned to direct gas in front of curved entrance mirror 126 and inlet port 120a is positioned to direct gas in front of curved output mirror 128.

Rod 122 is positioned between curved mirrors 126 and 128 such that the longitudinal axis of rod 122 is aligned with optical axis 110c. Rod 122 includes entrance aperture 122a to receive optical beam 108a passing through curved entrance mirror 126 and exit aperture 122b to output optical beam 110d through curved exit mirror 128, as shown in FIG. 2. Entrance aperture 122a and exit aperture 122b are aligned along the longitudinal axis of rod 122 to allow optical beam 110c to pass through rod 122. Rod 122 further includes linear slot 122c having a predetermined width and extending along a predetermined length on rod 122 to encompass optical cavity 110e. Slot 122c provides a linear opening in rod 122 along a transverse direction. Dimensions of rod slot 122c is such that optical beam 110d pass through the middle of slot 122c and the optical sensing region within slot 122c. The width of slot 122c is set such that the optical sensing region within slot 122c is not perturbed by interactions of the sample gas flow with the inside walls of slot 122c, and such that slot 122c is capable of being closed by tube 124. In one embodiment of the present invention, width of slot 122c is 0.3493 inch for a 0.678 inch diameter rod. In another embodiment of the present invention, width of slot 122c is 1 inch for a 1.9 inches diameter rod.

Tube 124 is concentric with and surrounds rod 122 such that tube 124 is capable of concentric rotation around rod 122. Tube 124 includes linear slots 124a and 124b having a predetermined width and extending along a predetermined length on tube 124. In one embodiment of the present invention, width of slots 124a and 124b is equal to width of slot 122c. Slots 124a and 124b are positioned opposing each other on the sides of tube 124 to provide a linear opening in tube along a transverse direction and to form a pass-through slot. In some embodiments of the present invention, tube 124 is an aluminum tube anodized to reduce friction caused by galling between the inner and outer aluminum parts, and improve the seal with rod 122.

Figure 3A:
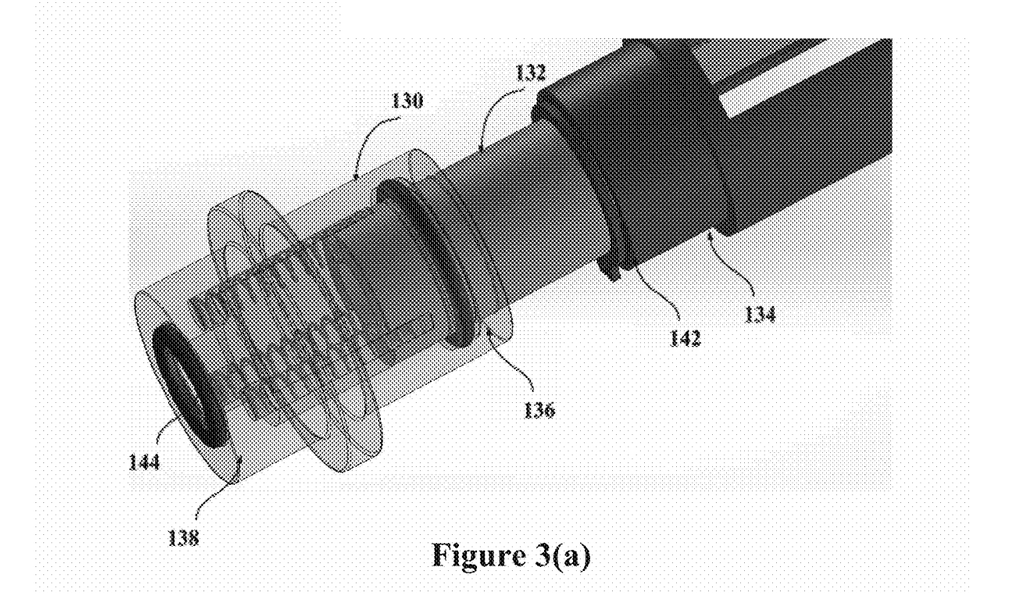
FIG. 3(a) illustrates a spring-loaded bearing and bushing assembly for an optical cell in accordance with one embodiment of the present invention.
Figure 3B:
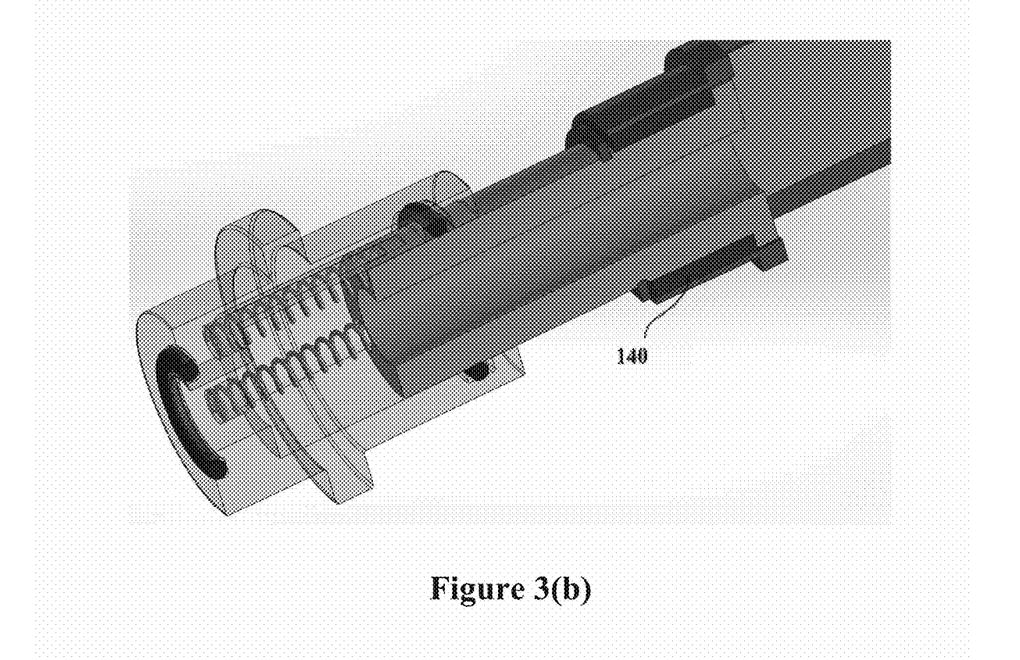
FIG. 3(b) is a cutaway view of FIG. 3(a) illustrating a spring-loaded bearing and bushing assembly for an optical cell in accordance with one embodiment of the present invention.

Referring to FIGS. 3(a) and 3(b), in some embodiments, rod 122 or tube 124 include an o-ring groove around each slot to improve the seal. The o-ring groove may have a dovetail shape to hold the o-ring. In other embodiments, rod 122 may be slightly elliptical to improve the seal and provide less friction than a circular shape. In another embodiment of the present invention, an air-tight spring-loaded bearing 130 is included to support rod 122 and tube 124, and to maintain a sealed chamber when tube 124 is in the closed position, as shown in FIGS. 3(a) and 3(b). Spring-loaded bearing 130 holds tube shutter assembly 132 and 134 for tube 124 in place, and provides a sliding seal 136 and a face seal 138 to eliminate intrusion of particles into mirror chambers 118 and 120 during zeroing. In one embodiment, face seal 138 is an o-ring that presses against the metal plate (not shown) that houses one of the mirrors.

Shutter assembly 132-134 further includes axial bushing 140 (shown in FIG. 3(b)) and snap-ring 142. Axial bushing 140 (e.g., Delrin bushings) is incorporated to reduce friction between tube 124 and rod 122 during rotation of tube 124. Snap-ring 142 counteracts any axial displacement of tube shutter 134 and/or bushing 140 due to slight misalignment of a linkage which transmits the force from a servo motor to turn tube 124 to the closed position during zeroing. The mechanism shown in FIGS. 3(a) and 3(b) further ensures that the purge flow is directed through the axial hole 144 (along the direction of the laser), thereby preventing particles in the sample gas flow from contaminating mirrors 126 and 128.

Figure 4A:
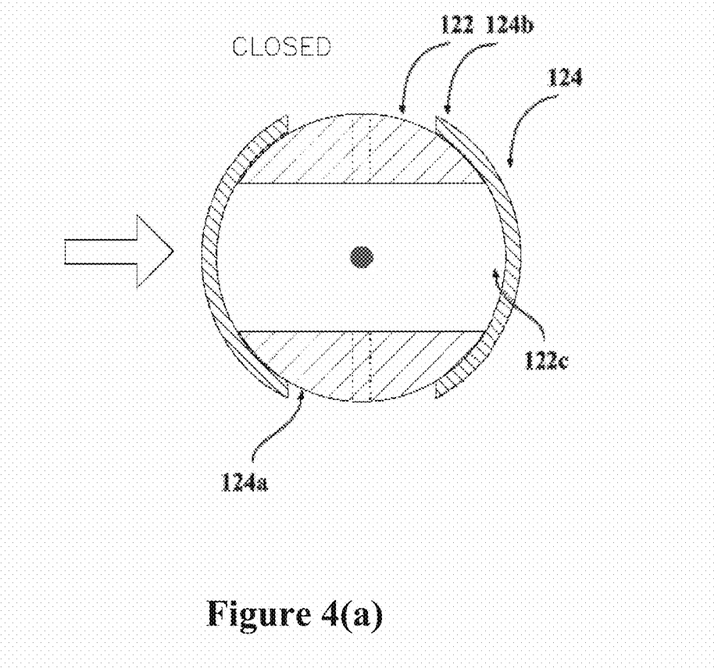
FIG. 4(a) is a cross-section view illustrating the optical cell in accordance with one embodiment of the present invention where rotating tube 124 is in the open position.
Figure 4B:
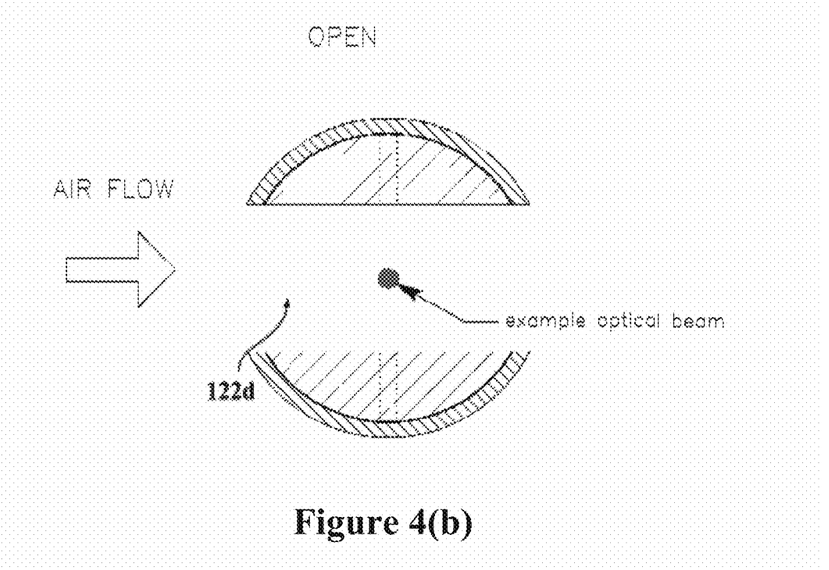
FIG. 4(b) is a cross-section view illustrating the optical cell in accordance with one embodiment of the present invention where rotating tube 124 is in the closed position.

Referring to FIGS. 4(a) and 4(b), by rotating tube 124 clockwise or counter-clockwise, and concentrically around rod 122, slots 124a and 124b can be simultaneously aligned with linear slot 122c on rod 122 to form a pass through slot 122d, as shown in FIG. 4(b), or misaligned with linear slot 122c on rod 122 to seal slot 122c. In one embodiment of the present invention, rotating tube 124 by about 90 degrees aligns the slots 124a and 124b with rod slot 122c to form a pass-through slot 122d. In some embodiments of the present invention, tube 124 includes at least one exit port located at the center of tube 124, and perpendicular to slots 124a and 124b, for purging a gas received into optical cell 110 via ports 118a and 120a.

Figure 5A:
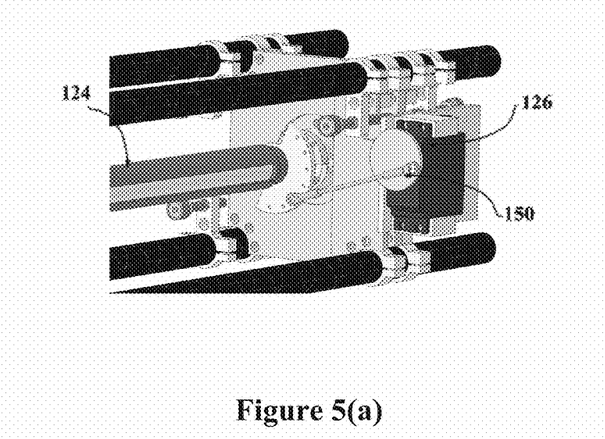
FIG. 5(a) illustrates an exemplary assembly for opening and closing the optical cell in accordance with an embodiment of the present invention using a servo motor.
Figure 5B:
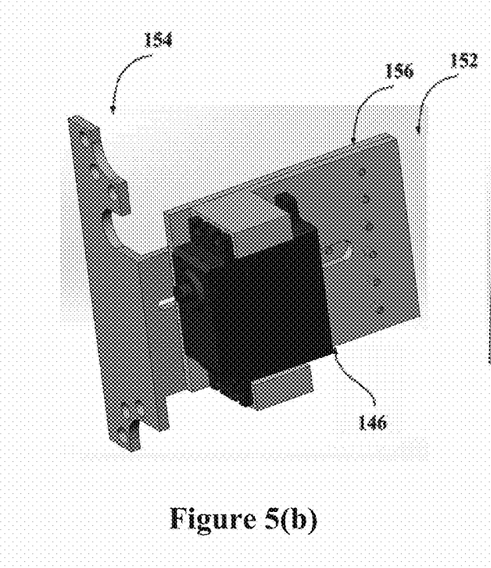
FIG. 5(b) is a front perspective view illustrating an exemplary assembly for opening and closing the optical cell in accordance with an embodiment of the present invention illustrating an exemplary three-piece aluminum mount used to attach a servo to the system.
Figure 5C:
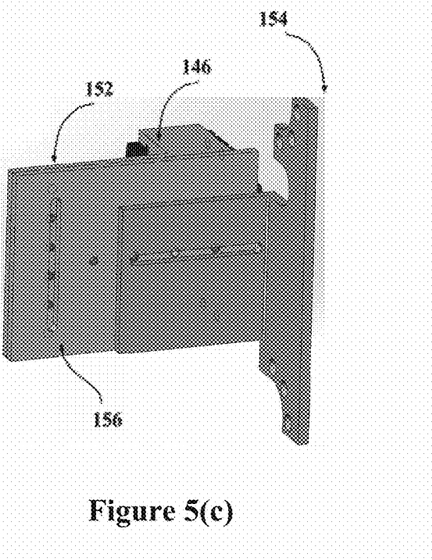
FIG. 5(c) is a rear perspective view illustrating an exemplary assembly for opening and closing the optical cell in accordance with an embodiment of the present invention illustrating an exemplary three-piece aluminum mount used to attach a servo to the system.

Referring to FIGS. 5(a)-5(c), in one embodiment of the present invention, rotation of tube 124 can be achieved using a servo motor 146 attached to tube 124 via a semi-circular flange 148 and threaded rod linkage 150, as shown in FIG. 5(a). Servomotor 146 must be accurately positioned in order to ensure that tube 124 turns smoothly and accurately into position (for zeroing or for sampling) when the servo is actuated. Positioning of servomotor 146 can be achieved with mounts capable of adjusting the position of servo motor 146 in at least two axes. FIGS. 5(b) and 5(c) illustrate an exemplary three-piece aluminum mount 152, 154 and 156 used to attach servo 146 to system 100. The design of the mount makes it possible to adjust servo 146 position along two axes. The three-piece mount shown in FIGS. 5(b) and 5(c) allows adjusting the position of servo 146 and locking servo 146 in position with screws (not shown) inserted into tapped holes 158 on mount 152.

Figure 6:
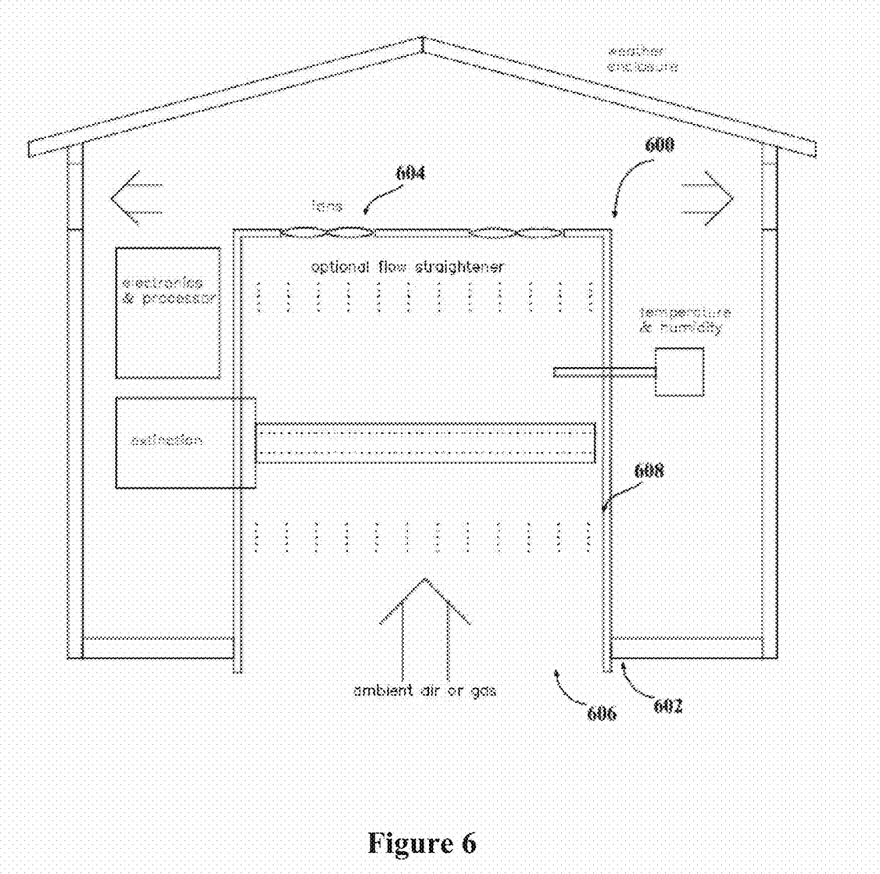
FIG. 6 illustrates an exemplary housing to accommodate the optical cell in accordance with an embodiment of the present invention.

Embodiments of the present invention further include a housing 600, as shown in FIG. 6, for accommodating optical cell 110. In one embodiment of the present invention, housing 600 is a duct surrounding optical cell 110 and having rectangular cross-section with an open bottom end 602, as further shown in FIG. 6. Exemplary housing 600 for accommodating optical cell 110 includes an aluminum duct of rectangular cross-section having a length of about 0.364 meters, width of about 0.040 meters and height of about 0.51 meters. Housing 600 includes at least one fan 604 positioned at the upper end of housing 600 to draw ambient air from bottom end 602 of housing 600 through vertically-oriented slot 606.

In one embodiment of the present invention, housing 600 includes nine 12-volt DC axial fans rated at 170 L/minute each positioned at the upper end of housing 600 to draw ambient air from the open bottom end 602 through vertically-oriented slot 606 having a length of about 0.0089 meters and a width of about 0.3493 meters. Housing 600 further includes a flow straightener 608 positioned at bottom end 602 to reduce turbulence in optical cell 110. An exemplary flow straightener is an aluminum honeycomb including multiple cells with each cell having length of about 0.064 meters on each side to form a flow straightener having an overall length of about 0.057 meters. In embodiments of the present invention utilizing housing 600, system 100 is protected from exposure to the weather on all sides by a polycarbonate enclosure. In such embodiments, housing bottom 602 protrudes through a cutout at the bottom of the enclosure to admit ambient air to optical cell 110.

During typical operation of open-path aerosol extinction system 100, light source 102 emits a continuous-wave laser for generating primary optical beam along path 102a. The continuous-wave laser generated by laser source 102 may be periodically turned on and off, or modulated, for pulsed operation. The wavelength of optical beam 102a is chosen to minimize interference in optical signal due to absorption from common atmospheric constituents. In one embodiment of the present invention, light source 102 emits a multi-mode continuous-wave diode laser (e.g., Power Technology, Little Rock, Ark., USA) centered at 674 nm. The wavelength of 674.22 nm is chosen to minimize interference in aerosol extinction signal due to absorption from common atmospheric constituents such as water. Water has a local minimum in its absorption at 674 nm, and by using a laser having a wavelength of about 674.22 nm, the sum of the absorption due to water (at 21° C. dew point), $O_3$ (100 ppb) and $NO_2$ (8 ppb) is minimized to less than 0.75 $Mm^{-1}$.

Optical beam 102a from light source 102 is directed to optical isolator 106 by optical component 104. Optical isolator 106 eliminates laser feedback caused by back reflections into optical beam 104a, and controls the polarization of optical beam along path 104a. An exemplary isolator that can be used to eliminate laser feedback includes a Faraday isolator (e.g., model TO-5-670-VLP, Thorlabs, Newton, N.J., USA). After passing through optical isolator 106, optical beam 106a is coupled directly into the optical cavity of optical cell 110 by optical component 108 with or without mode-matching optics.

Optical beam 108a enters the optical cavity of optical cell 110 through the aperture in curved entrance mirror 126 and entrance aperture 122a of rod 122. Optical beam 108a enters the optical cavity perpendicular to mirror 126, and is reflected by mirror 128 back along the incident path of optical beam 110c into the optical cavity of optical cell 110. Since mirrors 126 and 128 are highly reflective, optical beam 110c makes multiple round trips with minimal loss in amplitude per pass.

During sampling mode, sample gas is introduced into rod slot 122c by rotating tube 124 to align tube slots 124a and 124b with rod slot 122c. Aligning tube slots 124a and 124b with rod slot 122c allows a transverse airflow through slot 122c. The transverse airflow through slot 122c can be induced by a fan, wind, motion of an aircraft or other vehicle, and the like. In some embodiments of the present invention, tube 124 is rotated by a servo motor controlled by processor 116. When the sample interferes with the path of optical beam 110d in the optical sensing region, intensity of optical beam 110c decays exponentially due to absorption by species in sample gas. Time taken for optical beam 110c to exponentially decay from its initial intensity is measured as the "ringdown" time, and this ringdown time ($\tau$) can be used to calculate the concentration of the absorbing substance in the gas mixture in the optical cavity. In one embodiment of the present invention, light loss from the optical cavity may be measured using phase-shift methods, where the loss is measured by the phase shift of a sinusoidal. In another embodiment of the present invention, light loss from the optical cavity may be measured using other signal, or total light collection, where the cavity loss is measured from the total amount of light transmitted.

Referring again to FIG. 1, open-path aerosol extinction system 100 in accordance with an embodiment of the present invention further includes collimator 112 for collecting optical beam 110d exiting the optical cavity through an aperture in curved mirror 128. Collimator 112 is located behind the curved mirror 128 and is aligned to focus the collected optical beam 110d into a fiber optic cable that delivers optical beam 112a to photodetector 114. Processor 116 is positioned in communication with photodetector 114 to collect the optical signal from photodetector 114. In one embodiment of the present invention, processor 116 comprises a data acquisition system built around a single board computer. Exemplary single board computer includes a sbRIO 9636 (National Instruments, Austin, Tex.) which consists of a 400 MHz processor hosting a real-time operating system and a field programmable gate array (e.g., FPGA, Xilinx Sparan-6 LX45, San Jose, Calif.). Because exponential decay times can be in the range from about 10 µs to about 200 µs, digitization of photodetector 114 signal requires significantly more bandwidth (e.g., ~2 MHz) than that provided by the built in analog inputs. A circuit board containing a high speed digitizer (e.g., LTC2203, Linear Technology, Milpitas, Calif.) can be used for acquiring a 16-bit analog input signal at a rate of about $25 \times 10^6$ samples per second.

During measurements of the ringdown time ($\tau$), tube 124 is rotated by the servo motor controlled by processor 116 such that rod slot 122c is closed, thereby isolating optical cell 110 from ambient air. In some embodiments of the present invention, during measurements of the ringdown time, tube 124 is rotated by about 90 degrees by a servo motor controlled by processor 116 and linkage such that rod slot 122c is closed, thereby isolating optical cell 110 from ambient gas. In one embodiment of the present invention, optical cell 110 is isolated from ambient gas for about 2 minutes at a frequency of about every 20 minutes and then opened again for introducing sample gas into rod slot 122c. In embodiments of the present invention utilizing housing 600, when optical cell 110 is in sampling mode, axial fans 604 positioned at the upper end of housing 600 draw ambient air from the open bottom end 602 of housing 600 through the vertically-oriented slot 606 in housing 600. Flow straightener 608 located at the entrance of slot 606 reduces turbulence in optical cell 110.

During measurements of ringdown time ($\tau$), dry zero air is introduced via ports 118a and 120a, which flows continuously in front of each of mirrors 126 and 128 to prevent contamination of the highly reflective surfaces. In one embodiment of the present invention, filtered (e.g., 99.99% at 0.01 µm, Balston BQ, Haverhill, Mass.) ultrazero air (e.g., Scott-Marin, Riverside, Calif.), regulated at 0.1 L $min^{-1}$ by a mass flow controller (e.g., Alicat MC-1SLPM-D-24V, Tucson, Ariz.) is introduced via ports 118a and 120a, which flows continuously in front of each of mirrors 126 and 128 to prevent contamination of the highly reflective surfaces. In one embodiment of the present invention, while measuring extinction coefficient of ambient air, dry and filtered air, regulated at 0.05 L $min^{-1}$ by a mass flow controller (e.g., Alicat MC-1SLPM-D-24V, Tucson, Ariz., USA), flows continuously in front of mirrors 126 and 128 to prevent contamination of the highly reflective surfaces. The dry zero air (purge air) flows from chambers 118 and 120 directly into the optical cavity of optical cell 110. The dry-air flow constitutes only about 0.06% of the flow through optical cell 110; therefore, no corrections are made for the dilution of the ambient aerosol concentration in optical cell 110. The dry-air flow reduces the path length exposed to aerosol, and this effect is included in the open-path aerosol extinction coefficient calculation, as represented by RL in Equation (1).

Before opening rod slot 122c to ambient air in each open-close cycle, sample gas is purged from optical cell 110 by increasing flow rate of dry zero air introduced via ports 118a and 120a (zeroing mode). When optical cell 110 is in such zeroing mode, particle-free ringdown time ($\tau_0$) is measured by: (1) covering rod slot 122c so that optical cell 110 is isolated from ambient air flow; and (2) increasing the purge flow rate to about 0.8 L $min^{-1}$. The positive particle-free air pressure thus induced in optical cell 110 purges the particles in about 1 minute. In embodiments of the present invention utilizing housing 600, during zeroing mode axial fans are also turned off to avoid ambient air from leaking into optical cell 110. Particle-free ringdown times ($\tau_0$) are then recorded during the second minute of the 2-minute zeroing cycle. Relative humidity (RH) is measured using a thermo-hygrometer (e.g., HMP110, Vaisala, Vantaa, Finland) placed in housing 600 at about 0.25 m above optical cell 110. A hot wire anemometer, positioned at approximately the same height above optical cell 110 as the hygrometer, measures air velocity.

Optical beam 110d exiting the optical cavity through curved mirror 128 is focused into photodetector 114 by collimator 112. In one embodiment of the present invention, collimator 112 collects light escaping the optical cavity through mirror 128 and focuses it into a fiber optic cable. The fiber optic cable transmits light to photodetector 114 (e.g., HC120-05-MOD, Hamamatsu, Hamamatsu City, Shizuoka Pref., Japan), which is protected from ambient light by a narrow bandpass (10 nm full width at half maximum) filter centered at about 676 nm (e.g., Edmund Optics, Barrington, N.J., USA). Photodetector 114 transforms the power of optical beam 112a into an electric signal, which is recorded by a processor 116. In some embodiments of the present invention, measurement of transmitted optical beam 112a by photodetector 114 is synchronized with the operation of the laser source 102. In an exemplary embodiment, the signal acquired by photodetector 114 is synchronized with laser source 102 (typically operated at 1 kHz)—when the laser is switched off, processor 116 begins to acquire data from photodetector 114. The signal is acquired for a predetermined period generally not exceeding half of the time between pulses (e.g., 500 µs for a 1 kHz laser repetition rate).

Processor 116 determines the temporal decay of optical beam 110c by monitoring the weak transmission of optical beam 110d exiting the optical cavity through curved mirror 128. If some fraction of optical beam 110c is absorbed or scattered by gas molecules and/or particles in the optical cavity, the light transmission decreases more rapidly. The transmitted intensity of optical beam 110d decays exponentially at a rate which reflects the total cavity losses, including absorption losses. The aerosol extinction coefficient $\alpha$ is a function of the exponential decay time with and without particles in the cavity ($\tau$ and $\tau_0$, respectively) and is expressed by $$\alpha = \frac{R_L}{c}\left(\frac{1}{\tau} - \frac{1}{\tau_0}\right) \quad (1)$$

where c is the speed of light and $R_L$ is the ratio of the cavity length, a, to the sample length, b (see FIG. 1).

Figure 7:
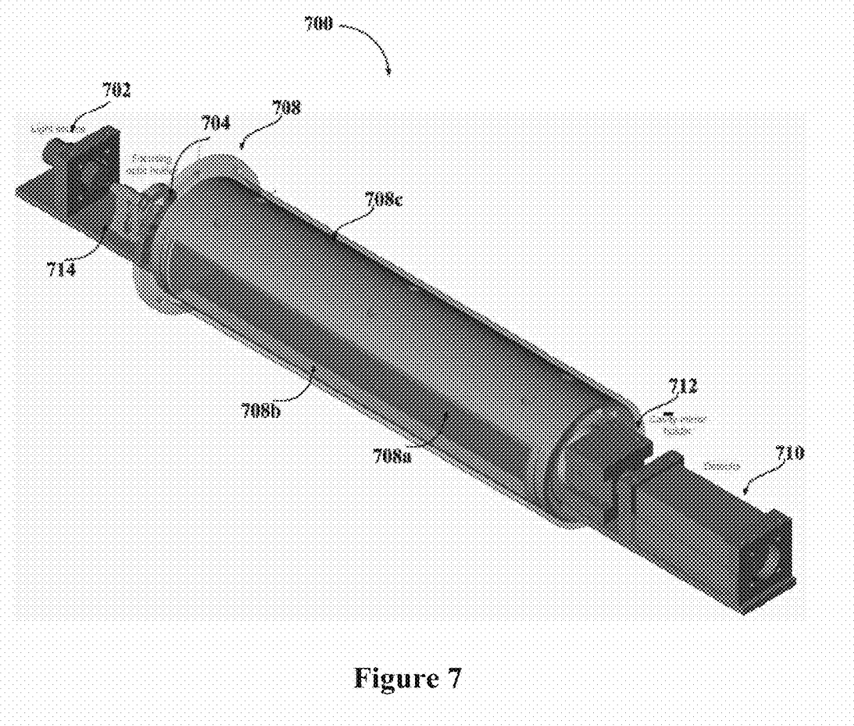
FIG. 7 illustrates an alternate embodiment of an open-path aerosol extinction system for measuring trace species in a sample gas.

Referring now to FIG. 7, there is shown a miniature open-path aerosol extinction system for measuring trace species in a sample gas, generally designated 700, which comprises an alternate embodiment of the present invention. Open-path aerosol extinction system 700 includes light source 702, lens 704, polarizer 706 (not shown), optical cell 708, photodetector 710, top plate 712, and bottom plate 714. Exemplary light source 702 that can used to generate primary optical beam include a small laser, light emitting diode, and the like. In open-path aerosol extinction system 700, light source 702, lens 704, polarizer 706, optical cell 708, and photodetector 710 are mounted on bottom plate 714 and top plate 712. Plates 712 and 714 sandwich light source 702, lens 704, polarizer 706, optical cell 708 and photodetector 710, and act as a beam to provide stiffness to open-path aerosol extinction system 700.

Open-path aerosol extinction system 700 includes a quarter-turn zeroing mechanism in a manner described above for other embodiments of the present invention. Plates 712 and 714 define a cavity 708a in optical cell 708 for accommodating sample gas, and a flow path through sample cavity 708a in optical cell 708, in a manner similar to rod assembly described earlier for other embodiments of the present invention. Plates 712 and 714 further hold inner cylinders 708b and outer cylinder 708c that provide the zeroing mechanism described earlier. Cylinders 708b and 708c are constructed from lightweight polymers such that they do not compete with the structural stability provided by plates 712 and 714. The curved surface on inner cylinder 708b includes a dovetail O-ring groove to provide a seal when cavity 708a within optical cell 708 is isolated from ambient air.

Reference now to a specific example which follows will provide a clearer understanding of systems in accordance with embodiments of the present invention. The example should not be construed as a limitation upon the scope of the present invention.

EXAMPLE

An open-path cavity ring down spectrometer (OPCRDS) for use on a 300 meter high instrumented tower was designed and manufactured. The OPCRDS and a 3-wavelength nephelometer (TSI 3563, Shoreview, Minn.) were installed on a remote-controlled equipment carriage (2 m×3 m×2 m steel enclosure) atop a 300 m instrumented tower, at National Oceanic and Atmospheric Administration's (NOAA) Boulder Atmospheric Observatory (BAO), during a Front Range Air Pollution and Photochemistry Experiment (FRAPPE). These instruments profiled ambient extinction and scattering between ground level and 285 meters above ground level (AGL). The nephelometer was mounted inside of the carriage, and a 2 m long×0.025 m diameter aluminum tube extending 1 m outside the carriage served as the nephelometer inlet. The flow rate through the nephelometer was 30 L min$^{-1}$. The inlet tubing was heated to 45° C. by wrapping the aluminum tubing with heat tape connected to a PID temperature controller; while this reduced the RH of the aerosol entering the nephelometer, no direct control over the aerosol RH was maintained. During normal operation, the nephelometer was zeroed for 5 minutes every hour. The nephelometer was calibrated before and after FRAPPE using the facility and protocol developed for nephelometer measurements at NOAA's long-term baseline observatories, and the average errors between the calibrations were statistically indistinguishable: 0.82% before and 1.05% after.

The OPCRDS was bolted to a custom steel frame on the outside of the carriage that extended ~0.5 m from the carriage wall. The nephelometer inlet and the OPCRDS were located within 1 m of each other. The particle-free ringdown $\tau_0$ was measured for 2 minutes every 20 minutes, and values between each $\tau_0$ measurement were linearly interpolated in time.

Extinction was calculated from 1 s averaged ringdowns as follows: (1) the contribution of Rayleigh scattering variability to the measured $\tau$ and $\tau_0$ was eliminated by correcting these parameters to a common temperature and pressure; (2) extinction was calculated using equation (1); and (3) extinction was corrected to standard temperature and pressure (STP, 273.15 K and 1000 mb) for comparison with the nephelometer. The contribution of water, $O_3$ and $NO_2$ to extinction were not significant and were not subtracted from the reported aerosol extinction.

The 1 s dry scattering values are calculated from the nephelometer data as follows: (1) the total scattering at 700 nm is calculated from $$C_{ts,700} = C_{700} \cdot (a_{700} + b_{700} \cdot \text{Å}) \quad (2)$$

where C700 is the measured scattering at 700 nm, $a_{700}$ is a factor that accounts for the truncation of the scattered radiation at scattering angles <7 degrees, $b_{700}$ is a correction factor accounting for the slightly non-cosine weighted light intensity in the nephelometer and Å is the Ångström exponent calculated from the scattering at 550 nm and 700 nm. The values chosen for $a_{700}$ and $b_{700}$ (1.297 and −0.113, respectively) are those recommended in Anderson and Ogren (Anderson and Ogren, *Determining Aerosol Radiative Properties Using the TSI* 3563 *Integrating Nephelometer*, Aerosol Science and Technology, 29:57-69, 1998) for non-size selected aerosol, since there was no impactor upstream of the nephelometer; (2) $C_{ts,700}$ is corrected to STP and (3) the scattering at 674 nm (to match the OPCRDS laser wavelength) is calculated using the Angstrom equation and the STP-corrected $C_{ts,700}$ FIGS. 8(*a*)-8(*d*) illustrate data accumulated during measurements made during a 2.5 h period of heavy cloud cover and rain demonstrate the OPCRDS's utility in extremely high RH conditions. Intermittent heavy cloud cover and precipitation are visible between Jul. 30, 2014 23:25 and Jul. 31, 2014 00:40 in the high spectral resolution lidar (Shipley et al. *High spectral resolution lidar to measure optical scattering properties of atmospheric aerosols*, Applied Optics (22)23: 3725-32, December 1983) image shown in FIG. 8(*a*). The aerosol entering the nephelometer was dried (<65%); therefore, scattering was relatively constant even when sampling in clouds (FIG. 8(*b*)). However, the OPCRDS extinction peaks during the cloud sampling periods due to the highly humidified aerosol. Several isolated clouds (visible in FIG. 8(*a*) and enlarged in FIG. 8(*c*)) intersect the OPCRDS and nephelometer at 285 meters AGL for ~1 minute, causing the ambient extinction to peak above 300 $Mm^{-1}$ (enlarged in FIG. 8(*d*)) while the dry scattering value remained constant.

Figure 8A:
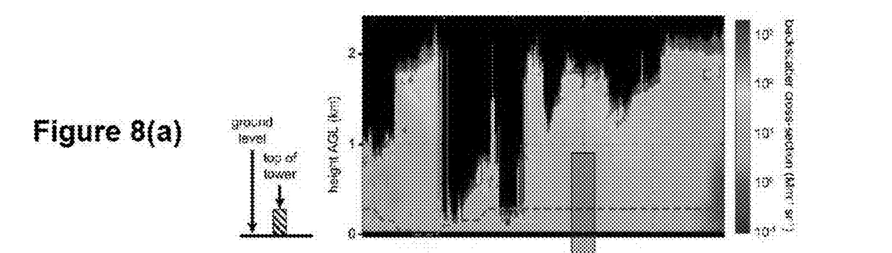
FIG. 8(a) illustrates exemplary data from measurements performed using an open-path aerosol extinction system in accordance with an embodiment of the present invention, where intermittent heavy cloud cover and precipitation are visible between Jul. 30, 2014 23:25 and Jul. 31, 2014 00:40 in the high spectral resolution lidar.
Figure 8B:
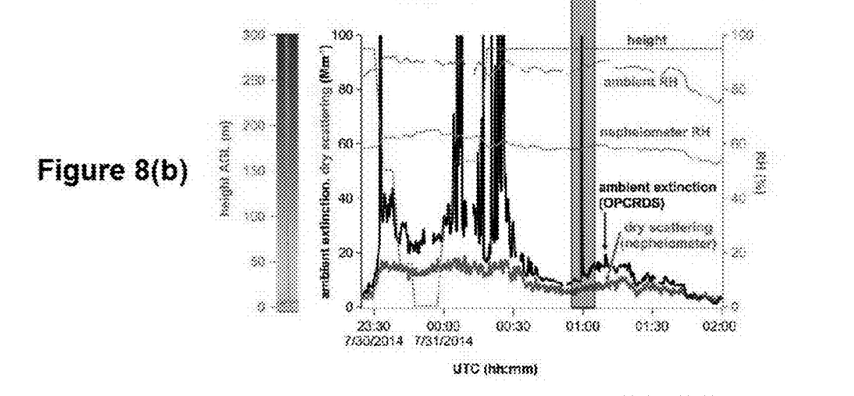
FIG. 8(b) illustrates exemplary data from measurements performed using an open-path aerosol extinction system in accordance with an embodiment of the present invention where the aerosol entering the nephelometer was dried (<65%); therefore, scattering was relatively constant even when sampling in clouds.
Figure 8C:
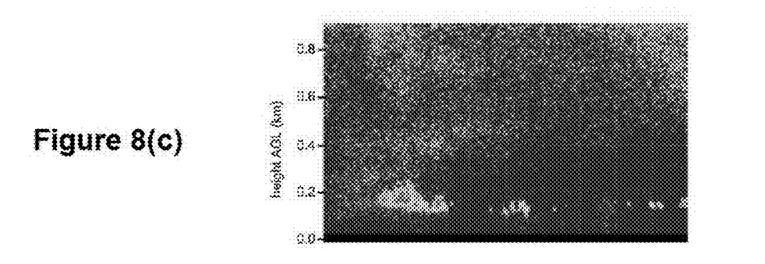
FIG. 8(c) illustrates exemplary data from measurements performed using an open-path aerosol extinction system in accordance with an embodiment of the present invention where several isolated clouds visible in FIG. 8(a) are enlarged in FIG. 8(c).
Figure 8D:
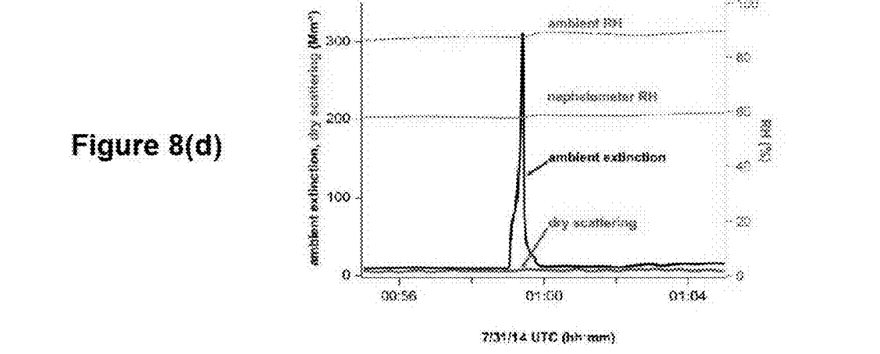
FIG. 8(d) illustrates exemplary data from measurements performed using an open-path aerosol extinction system in accordance with an embodiment of the present invention where the several isolated clouds enlarged in FIG. 8(c) intersect the OPCRDS and nephelometer at 285 meters AGL for ~1 minute, causing the ambient extinction to peak above 300 $Mm^{-1}$ while the dry scattering value remained constant.

Assuming no absorbing species were present, the ratio of extinction at high RH to extinction at low RH, f(RH), calculated during the 1-minute cloud intersection at 00:59:03 UTC ranged from 1.7 to 58.1 (mean=12.1 and σ=13.8). The extremely high values at the peak are indicative of highly humidified particles and/or droplets. Note that the OPCRDS's fast time response makes it possible to resolve some structure in the rising and falling seconds of the peak in FIG. 8(*d*). At 01:45 when the rain clears (evident in the transition from green to blue in the bottom right corner of FIG. 8(*a*)) and the ambient RH drops below 90%, the extinction and scattering are approximately equal. This behavior is consistent with the well-known steep increase in f(RH) above 90% RH.

The ambient RH data reported in FIGS. 8(*a*)-(*d*) were recorded by a sensor in the center of the OPCRDS duct ~21.5 cm above the optical cavity. A small increase in the RH during the cloud sampling period (00:59:03 UTC) is visible in FIG. 8(*d*), but the lack of a large, distinct RH spike is due to the fact that the response time for the sensor when subjected to a step change in RH from 90% to 100% is many minutes. Since the OPCRDS was in the cloud (FIGS. 8(*c*)-8(*d*)) for only one minute, the sensor would not have had enough time to reach steady state, and the measured RH would be lower than the actual value in the cloud. In addition, the average temperature in the duct was stable and −0.8 K higher than the value reported by a sensor on the BAO tower 15 m above the OPCRDS (the OPCRDS was positioned at 285 m during this time period). This tower sensor reported an average RH of 95.1% between 00:30 and 01:30 UTC at 300 m AGL, but if the temperature were 0.8 K higher (as in the duct), the RH would drop to approximately 91%, which is closer to the value reported by the sensor in the duct.

During the field study at NOAA's Boulder Atmospheric Observatory, the OPCRDS recorded very large extinction enhancement (f(RH)>50) due to highly humidified aerosol and/or droplets in low-lying rain clouds, demonstrating the utility of the OPCRDS in extremely high RH conditions.

Systems in accordance with embodiments of the present invention can be applied in various ways. System and methods in accordance with one or more embodiments of the present invention can be utilized by industries where extinction can be used to quantify the amount of indoor or outdoor pollution. Extinction is closely related to visibility, which is subject to government regulation. In an exemplary application, embodiments of the present invention can be used to monitor pollution conditions near solar arrays. In addition to its utility in characterizing aerosols, embodiments of the present invention could also be employed to study gases that are too sticky or reactive to be sampled in a closed-path instrument. The short residence time of the air in the instrument make it useful for measuring particle flux (e.g., using eddy covariance methods), since such measurements have been limited in the past due to technical difficulties in measuring aerosol at high enough time resolution (10-20 Hz). An Open-path aerosol extinction system in accordance with embodiments of the present invention is capable of being deployed on a research aircraft. Vertical aerosol extinction profiles from deployment on an aircraft-based open-path aerosol extinction system could help further constrain ground- and satellite-derived aerosol optical depth (AOD) retrievals and the radiative forcing uncertainty in twilight zones around clouds and in coarse dust-dominated regions.

Systems in accordance with embodiments of the present invention has several advantages over previous CRDS spectrometers. More particularly, geometry of the system in accordance with embodiments of the present invention has several advantages over previous designs: (a) open-path aerosol extinction system avoids the confounding effect of possible concentration gradients between the light source and its distant target; (b) a more localized (and therefore well-defined) sample is analyzed in open-path aerosol extinction system; and (c) background signal can be easily minimized by zeroing the instrument. It is thought that the open-path aerosol extinction system of the present invention and many of its attendant advantages will be understood from the foregoing description and it will be apparent that various changes may be made in the form, construction arrangement of parts thereof without departing from the spirit and scope of the invention or sacrificing all of its material advantages, the form hereinbefore described being merely a preferred or exemplary embodiment thereof.

We claim:
1. A system for measuring trace species in a sample gas, said system comprising:
 a laser source for emitting continuous wave laser beam;
 an optical isolator for allowing transmission of the laser beam in one direction;

a plurality of input mirrors for directing the laser beam into an optical cavity;
a first curved mirror located at a first end and a second curved mirror located at a second end, wherein the first and second curved mirrors face each other along a common optical axis to form the optical cavity;
a rod positioned between the first and second curved mirrors, wherein the longitudinal axis of the rod is aligned with the optical axis, wherein the rod comprises a linear slot encompassing the optical cavity, wherein the linear slot extends along a predetermined length on the rod along the longitudinal axis, wherein the linear slot is capable of receiving the sample gas, and wherein the rod comprises a first aperture and a second aperture to allow the laser beam received from the plurality of input mirrors to pass through the rod along the optical axis;
a tube concentric with and surrounding the rod, wherein the tube comprises a first linear slot and second linear slot, wherein the first and second linear slot oppose each other to form a pass-through slot; and
a photodetector for measuring light transmitted through the optical cavity and producing a corresponding signal.

2. The system of claim 1, wherein the optical cell further comprises:
a first mirror chamber for accommodating the first curved mirror and a second mirror chamber for accommodating the second curved mirror; and
a first and second inlet ports located on the first and second mirror chambers, wherein the first and second inlet ports are capable of receiving and directing calibrated gas in front of the first and second curved mirrors.

3. The system of claim 2, further comprising:
a housing for accommodating the first and second chamber, the rod and the tube, wherein the housing comprises a vertically oriented slot;
at least one fan positioned at a first end of the housing to draw ambient air from a second end of the housing through the vertically oriented slot in the housing, wherein the second end of the housing is open to the ambient air; and
a flow straightener positioned at the second end of the housing, wherein the flow straighteners is capable of reducing turbulence in the optical cavity.

4. The system of claim 2, further comprising at least one exit port located at the center of the tube and perpendicular to the first and second slots for purging the calibrated gas.

5. The system of claim 1, further comprising a fiber collimator located behind the second curved mirror for collecting laser beam exiting the optical cavity through the second curved mirror, wherein the collimator focuses the collected laser beam into a fiber optic cable, and wherein the fiber optic cable transmits the focused laser beam to the photodetector.

6. The system of claim 1, further comprising a processor, responsive to said signal from the photodetector, for calculating the decay rate of the optical cavity, wherein the processor, responsive to said decay rate, determines the level of trace species in said sample gas, and wherein the processor synchronizes the measuring of the transmitted light by the photodetector with operation of the laser source.

7. The system of claim 1, wherein the rod comprising the linear slot further comprises an optical sensing region along the optical axis within the linear slot, and wherein the optical sensing region and the walls of the linear slot are separated by a predetermined distance.

8. The system of claim 1, wherein the tube is capable of concentric rotation around the rod, and wherein the first and second slots are capable of simultaneously aligning with the linear slot on the rod.

9. The system of claim 1, wherein the tube is capable of concentric rotation around the rod, and wherein the first and second slots are capable of simultaneously misaligning with the linear slot on the rod to seal the linear slot on the rod from ambient air.

10. The system of claim 8, wherein the tube is capable of concentric rotation of about 90 degrees around the rod.

11. The system of claim 9, wherein the tube is capable of concentric rotation of about 90 degrees around the rod.

12. An open-path optical cell for measuring trace species in a sample gas, said cell comprising:
a first mirror chamber comprising a first curved mirror located at a first end of the optical cell and a second mirror chamber comprising a second curved mirror located at a second end of the optical cell, wherein the first and second curved mirrors face each other along a common optical axis to form an optical cavity;
a first and second inlet ports located on the first and second mirror chambers, wherein the first and second inlet ports are capable of receiving and directing calibrated gas in front of the first and second curved mirrors;
a rod positioned between the first and second curved mirrors, wherein the longitudinal axis of the rod is aligned with the optical axis, wherein the rod comprises a linear slot encompassing the optical cavity and extending along a predetermined length on the rod along the longitudinal axis, wherein the linear slot is capable of receiving the sample gas, wherein the rod comprises a first aperture to receive the laser beam from the first curved mirror and a second aperture to output the laser beam along the longitudinal axis to the second curved mirror, and wherein the first and second apertures allow the laser beam to pass through the rod along the optical axis; and
a tube concentric with and surrounding the rod, wherein the tube comprises a first linear slot opposing a second linear slot to form a pass through slot.

13. The optical cell of claim 12, wherein the rod comprising the linear slot further comprises an optical sensing region along the optical axis within the linear slot, and wherein the optical sensing region is not perturbed by the walls of the linear slot.

14. The optical cell of claim 12, wherein the tube is capable of concentric rotation around the rod, and wherein the first and second slots are capable of simultaneously aligning with the linear slot on the rod.

15. The optical cell of claim 12, wherein the tube is capable of concentric rotation around the rod, wherein the first and second slots are capable of simultaneously misaligning with the linear slot on the rod, and wherein the linear slot on the rod is sealed from ambient air.

16. The optical cell of claim 14, wherein the tube is capable of concentric rotation of about 90 degrees around the rod.

17. The optical cell of claim 15, wherein the tube is capable of concentric rotation of about 90 degrees around the rod.

18. The optical cell of claim 12, further comprising at least one exit port located on the tube and perpendicular to the first and second slots for purging the calibrated gas.

19. A system for measuring trace species in a sample gas, said system comprising:
- a light source for emitting an optical beam;
  - a first mirror chamber comprising a first curved mirror, wherein the first curved mirror is positioned to receive the optical beam;
  - a second mirror chamber comprising a second curved mirror, wherein the first and second curved mirrors face each other along a common optical axis to form an optical cavity;
  - a first and second inlet ports located on the first and second mirror chambers, wherein the first and second inlet ports are capable of receiving and directing calibrated gas in front of the first and second curved mirrors;
  - a first and second plates for mounting the light source and the first and second mirror chambers, wherein the first and second plates align the light source and the first and second curved mirrors along the optical axis;
  - a sample cavity formed between the first and second plates for receiving the sample gas, wherein the longitudinal axis of the sample cavity is aligned with the optical axis, wherein the sample cavity comprises a linear slot encompassing the optical cavity and extending along a predetermined length along the longitudinal axis, wherein the linear slot is capable of receiving the sample gas, wherein the sample cavity comprises a first aperture to receive the laser beam from the first curved mirror and a second aperture to output the laser beam along the longitudinal axis to the second curved mirror, and wherein the first and second apertures allow the laser beam to pass through the sample cavity along the optical axis;
  - a tube surrounding the first and second plates forming the sample cavity, wherein the tube comprises a first linear slot opposing a second linear slot to form a pass through slot; and
  - a photodetector mounted on the first plate for measuring light transmitted through the optical cavity and producing a corresponding signal.

20. The system of claim 17, further comprising a first and second inlet ports located on the first and second mirror chambers, wherein the first and second inlet ports are capable of receiving and directing calibrated gas in front of the first and second curved mirrors.

* * * * *